United States Patent
Bailly (10) Patent No.: US 10,213,283 B2
(45) Date of Patent: Feb. 26, 2019

(54) TEXTILE-BASED PROSTHESIS FOR LAPAROSCOPIC SURGERY

(71) Applicant: Sofradim Production, Trévoux (FR)

(72) Inventor: Pierre Bailly, Caluire-et-Cuire (FR)

(73) Assignee: Sofradim Production, Trevoux (FR)

( * ) Notice: Subject to any disclaimer, the term of this patent is extended or adjusted under 35 U.S.C. 154(b) by 102 days.

(21) Appl. No.: 14/784,073

(22) PCT Filed: Jun. 5, 2014

(86) PCT No.: PCT/EP2014/061655
§ 371 (c)(1),
(2) Date: Oct. 13, 2015

(87) PCT Pub. No.: WO2014/195389
PCT Pub. Date: Dec. 11, 2014

(65) Prior Publication Data
US 2016/0067029 A1    Mar. 10, 2016

(30) Foreign Application Priority Data
Jun. 7, 2013 (FR) .................................... 13 55261

(51) Int. Cl.
*A61F 2/00* (2006.01)
(52) U.S. Cl.
CPC .... *A61F 2/0063* (2013.01); *A61F 2002/0072* (2013.01); *A61F 2210/0004* (2013.01); *A61F 2220/0041* (2013.01); *A61F 2250/0097* (2013.01)

(58) Field of Classification Search
CPC ....................... A61F 2/0063; A61F 2002/0072
See application file for complete search history.

(56) References Cited

U.S. PATENT DOCUMENTS

| 1,187,158 | A | 6/1916 | Mcginley |
| 3,118,294 | A | 1/1964 | Van Laethem |
| 3,124,136 | A | 3/1964 | Usher |
| 3,272,204 | A | 9/1966 | Charles et al. |
| 3,276,448 | A | 10/1966 | Usher |
| 3,320,649 | A | 5/1967 | Naimer |

(Continued)

FOREIGN PATENT DOCUMENTS

| CA | 1317836 C | 5/1993 |
| DE | 19544162 C1 | 4/1997 |

(Continued)

OTHER PUBLICATIONS

International Search Report for PCT/EP14/061655 date of completion is Jul. 9, 2014 (3 pages).

(Continued)

*Primary Examiner* — Alexander Orkin (57) ABSTRACT

The invention relates to a prosthesis (1) comprising a textile (2) of elongate shape defining a longitudinal axis A, and a reinforcing element comprising at least one semi-rigid elongate structure (8) connected to said textile, said structure being substantially parallel to said longitudinal axis A and having a distal end provided with at least one fastening element (4) distinct from said textile and capable of cooperating with a part of a tool (10) that is able to pass through said trocar, in order to temporarily couple said prosthesis to said tool.

21 Claims, 3 Drawing Sheets

(56) References Cited

U.S. PATENT DOCUMENTS

| | | |
|---|---|---|
| 3,364,200 A | 1/1968 | Ashton et al. |
| 3,570,482 A | 3/1971 | Emoto et al. |
| 4,006,747 A | 2/1977 | Kronenthal et al. |
| 4,060,081 A | 11/1977 | Yannas et al. |
| 4,173,131 A | 11/1979 | Pendergrass et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 5,002,551 A | 3/1991 | Linsky et al. |
| 5,122,155 A * | 6/1992 | Eberbach .......... A61B 17/00234 606/1 |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,263,983 A | 11/1993 | Yoshizato et al. |
| 5,304,595 A | 4/1994 | Rhee et al. |
| 5,306,500 A | 4/1994 | Rhee et al. |
| 5,324,775 A | 6/1994 | Rhee et al. |
| 5,328,955 A | 7/1994 | Rhee et al. |
| 5,333,624 A * | 8/1994 | Tovey .................. A61B 17/0401 128/897 |
| 5,334,527 A | 8/1994 | Brysk |
| 5,339,657 A | 8/1994 | McMurray |
| 5,350,583 A | 9/1994 | Yoshizato et al. |
| 5,356,432 A | 10/1994 | Rutkow et al. |
| 5,368,549 A | 11/1994 | McVicker |
| 5,368,602 A * | 11/1994 | de la Torre ........ A61B 17/0057 602/44 |
| 5,376,375 A | 12/1994 | Rhee et al. |
| 5,376,376 A | 12/1994 | Li |
| 5,383,477 A * | 1/1995 | DeMatteis ......... A61B 17/0057 128/898 |
| 5,397,331 A | 3/1995 | Himpens et al. |
| 5,399,361 A | 3/1995 | Song et al. |
| 5,405,360 A * | 4/1995 | Tovey ............. A61B 17/00234 606/151 |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,681,568 A | 10/1997 | Goldin et al. |
| 5,686,115 A | 11/1997 | Voumakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,709,934 A | 1/1998 | Bell et al. |
| 5,716,409 A | 2/1998 | Debbas |
| 5,720,981 A | 2/1998 | Eisinger |
| 5,732,572 A | 3/1998 | Litton |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |
| 5,769,864 A | 6/1998 | Kugel |
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | McGregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |
| 5,910,149 A | 6/1999 | Kuzmak |
| 5,911,731 A | 6/1999 | Pham et al. |
| 5,916,225 A | 6/1999 | Kugel |
| 5,919,232 A | 7/1999 | Chaffringeon et al. |
| 5,919,233 A | 7/1999 | Knopf et al. |
| 5,922,026 A | 7/1999 | Chin |
| 5,931,165 A | 8/1999 | Reich et al. |
| 5,942,278 A | 8/1999 | Hagedorn et al. |
| 5,962,136 A | 10/1999 | Dewez et al. |
| 5,972,022 A | 10/1999 | Huxel |
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Kovac |

(56) References Cited

U.S. PATENT DOCUMENTS

| | | |
|---|---|---|
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,120,539 A | 9/2000 | Eldridge et al. |
| 6,132,765 A | 10/2000 | DiCosmo et al. |
| 6,143,037 A | 11/2000 | Goldstein et al. |
| 6,153,292 A | 11/2000 | Bell et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,197,325 B1 | 3/2001 | MacPhee et al. |
| 6,197,934 B1 | 3/2001 | DeVore et al. |
| 6,197,935 B1 | 3/2001 | Doillon et al. |
| 6,210,439 B1 | 4/2001 | Firmin et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,424 B1 | 10/2001 | Vyakarnam et al. |
| 6,312,474 B1 | 11/2001 | Francis et al. |
| 6,328,686 B1 | 12/2001 | Kovac |
| 6,334,872 B1 | 1/2002 | Termin et al. |
| 6,383,201 B1 | 5/2002 | Dong |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | DeVore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,500,464 B2 | 12/2002 | Ceres et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,551,356 B2 * | 4/2003 | Rousseau ............ A61F 2/0063 606/151 |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,610,006 B1 * | 8/2003 | Amid ............... A61F 2/0063 600/37 |
| 6,613,348 B1 | 9/2003 | Jain |
| 6,623,963 B1 | 9/2003 | Muller et al. |
| 6,630,414 B1 | 10/2003 | Matsumoto |
| 6,638,284 B1 | 10/2003 | Rousseau et al. |
| 6,652,594 B2 | 11/2003 | Francis et al. |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,719,795 B1 | 4/2004 | Cornwall et al. |
| 6,723,335 B1 | 4/2004 | Moehlenbruck et al. |
| 6,730,299 B1 | 5/2004 | Tayot et al. |
| 6,736,823 B2 | 5/2004 | Darois et al. |
| 6,743,435 B2 | 6/2004 | DeVore et al. |
| 6,755,868 B2 | 6/2004 | Rousseau |
| 6,773,723 B1 | 8/2004 | Spiro et al. |
| 6,783,554 B2 | 8/2004 | Amara et al. |
| 6,790,213 B2 | 9/2004 | Cherok et al. |
| 6,790,454 B1 | 9/2004 | Abdul Malak et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,893,653 B2 | 5/2005 | Abraham et al. |
| 6,896,904 B2 | 5/2005 | Spiro et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,988,386 B1 | 1/2006 | Okawa et al. |
| 7,025,063 B2 | 4/2006 | Snitkin et al. |
| 7,041,868 B2 | 5/2006 | Greene et al. |
| RE39,172 E | 7/2006 | Bayon et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,594,921 B2 | 9/2009 | Browning |
| 7,615,065 B2 | 11/2009 | Priewe et al. |
| 7,670,380 B2 | 3/2010 | Cauthen, III |
| 7,709,017 B2 | 5/2010 | Tayot |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,799,767 B2 | 9/2010 | Lamberti et al. |
| 7,806,905 B2 | 10/2010 | Ford et al. |
| 7,824,420 B2 | 11/2010 | Eldridge et al. |
| 8,142,515 B2 | 3/2012 | Therin et al. |
| 8,197,837 B2 | 6/2012 | Jamiolkowski et al. |
| 8,323,675 B2 | 12/2012 | Greenawalt |
| 8,366,787 B2 | 2/2013 | Brown et al. |
| 8,709,094 B2 | 4/2014 | Stad et al. |
| 8,846,060 B2 | 9/2014 | Archibald et al. |
| 8,877,233 B2 | 11/2014 | Obermiller et al. |
| 8,956,373 B2 | 2/2015 | Ford et al. |
| 9,034,357 B2 | 5/2015 | Stopek |
| 2002/0095218 A1 | 7/2002 | Carr et al. |

(56) References Cited

U.S. PATENT DOCUMENTS

| | | | |
|---|---|---|---|
| 2003/0086975 A1 | 5/2003 | Ringeisen | |
| 2003/0114937 A1 | 6/2003 | Leatherbury et al. | |
| 2003/0130745 A1 | 7/2003 | Cherok et al. | |
| 2003/0133967 A1 | 7/2003 | Ruszczak et al. | |
| 2003/0225355 A1 | 12/2003 | Butler | |
| 2004/0034373 A1 | 2/2004 | Schuldt-Hempe et al. | |
| 2004/0059356 A1 | 3/2004 | Gingras | |
| 2004/0101546 A1 | 5/2004 | Gorman et al. | |
| 2005/0002893 A1 | 1/2005 | Goldmann | |
| 2005/0021058 A1 | 1/2005 | Negro | |
| 2005/0085924 A1 | 4/2005 | Darois et al. | |
| 2005/0113849 A1 | 5/2005 | Popadiuk et al. | |
| 2005/0137512 A1 | 6/2005 | Campbell et al. | |
| 2005/0142161 A1 | 6/2005 | Freeman et al. | |
| 2005/0148963 A1 | 7/2005 | Brennan | |
| 2005/0171569 A1* | 8/2005 | Girard | A61B 17/00234 606/193 |
| 2005/0175659 A1 | 8/2005 | Macomber et al. | |
| 2005/0232979 A1 | 10/2005 | Shoshan | |
| 2005/0267521 A1 | 12/2005 | Forsberg | |
| 2005/0288691 A1 | 12/2005 | Leiboff | |
| 2006/0064175 A1 | 3/2006 | Pelissier et al. | |
| 2006/0135921 A1 | 6/2006 | Wiercinski et al. | |
| 2006/0147501 A1 | 7/2006 | Hillas et al. | |
| 2006/0216320 A1 | 9/2006 | Kitazono et al. | |
| 2006/0252981 A1 | 11/2006 | Matsuda et al. | |
| 2006/0259074 A1* | 11/2006 | Kelleher | A61B 17/04 606/213 |
| 2007/0088189 A1* | 4/2007 | Levy | A61B 17/42 600/37 |
| 2007/0299538 A1 | 12/2007 | Roeber | |
| 2008/0206305 A1* | 8/2008 | Herweck | A61L 31/10 424/423 |
| 2008/0306497 A1* | 12/2008 | Brown | A61F 2/0063 606/151 |
| 2011/0077457 A1* | 3/2011 | Deitch | A61F 2/0045 600/37 |
| 2012/0209301 A1* | 8/2012 | Bell | A61B 46/30 606/151 |
| 2013/0231526 A1* | 9/2013 | Felix | A61B 17/00234 600/37 |

FOREIGN PATENT DOCUMENTS

| | | |
|---|---|---|
| DE | 10019604 A1 | 10/2001 |
| DE | 10043396 C1 | 6/2002 |
| EP | 0194192 A1 | 9/1986 |
| EP | 0248544 A1 | 12/1987 |
| EP | 0276890 A2 | 8/1988 |
| EP | 0372969 A1 | 6/1990 |
| EP | 544485 A1 | 6/1993 |
| EP | 0552576 A1 | 7/1993 |
| EP | 614650 A2 | 9/1994 |
| EP | 0621014 A1 | 10/1994 |
| EP | 0625891 A1 | 11/1994 |
| EP | 0637452 A1 | 2/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 827724 A2 | 3/1998 |
| EP | 0836838 A1 | 4/1998 |
| EP | 0895762 A2 | 2/1999 |
| EP | 898944 A2 | 3/1999 |
| EP | 1017415 A1 | 7/2000 |
| EP | 1052319 A1 | 11/2000 |
| EP | 1055757 A1 | 11/2000 |
| EP | 1 216 717 A1 | 6/2002 |
| EP | 1 216 718 A1 | 6/2002 |
| EP | 0693523 B1 | 11/2002 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1782848 A2 | 5/2007 |
| FR | 2244853 A1 | 4/1975 |
| FR | 2257262 A1 | 8/1975 |
| FR | 2 308 349 A1 | 11/1976 |
| FR | 2453231 A1 | 10/1980 |
| FR | 2715405 A1 | 7/1995 |
| FR | 2 724 563 A1 | 3/1996 |
| FR | 2744906 A1 | 8/1997 |
| FR | 2766698 A1 | 2/1999 |
| FR | 2771622 A1 | 6/1999 |
| FR | 2779937 A1 | 12/1999 |
| FR | 2859624 A1 | 3/2005 |
| FR | 2863277 A1 | 6/2005 |
| FR | 2884706 A1 | 10/2006 |
| GB | 2 051 153 A | 1/1981 |
| JP | H0332677 A | 2/1991 |
| JP | H05237128 A | 9/1993 |
| JP | H09137380 A | 5/1997 |
| WO | 89/02445 A1 | 3/1989 |
| WO | 89/08467 A1 | 9/1989 |
| WO | 90/12551 A1 | 11/1990 |
| WO | 92/06639 A2 | 4/1992 |
| WO | 92/20349 A1 | 11/1992 |
| WO | 93/11805 A1 | 6/1993 |
| WO | 93/18174 A1 | 9/1993 |
| WO | 94/17747 A1 | 8/1994 |
| WO | 95/07666 A1 | 3/1995 |
| WO | 95/18638 A1 | 7/1995 |
| WO | 95/32687 A1 | 12/1995 |
| WO | 96/03091 A1 | 2/1996 |
| WO | 96/08277 A1 | 3/1996 |
| WO | 96/09795 A1 | 4/1996 |
| WO | 96/14805 A1 | 5/1996 |
| WO | 96/41588 A1 | 12/1996 |
| WO | 97/35533 A1 | 10/1997 |
| WO | 98/35632 A1 | 8/1998 |
| WO | 98/49967 A1 | 11/1998 |
| WO | 99/05990 A1 | 2/1999 |
| WO | 99/06079 A1 | 2/1999 |
| WO | 99/06080 A1 | 2/1999 |
| WO | 99/51163 A1 | 10/1999 |
| WO | 00/16821 A1 | 3/2000 |
| WO | 00/67663 A1 | 11/2000 |
| WO | 01/15625 A1 | 3/2001 |
| WO | 01/80773 A1 | 11/2001 |
| WO | 02/007648 A1 | 1/2002 |
| WO | WO 02/22047 A1 | 3/2002 |
| WO | 02/078568 A1 | 10/2002 |
| WO | 03/002168 A1 | 1/2003 |
| WO | 2004004600 A1 | 1/2004 |
| WO | 2004071349 A2 | 8/2004 |
| WO | 2004078120 A2 | 9/2004 |
| WO | 2004103212 A1 | 12/2004 |
| WO | 200511280 A1 | 2/2005 |
| WO | 2005013863 A2 | 2/2005 |
| WO | 2005018698 A1 | 3/2005 |
| WO | 2005105172 A1 | 11/2005 |
| WO | 2006018552 A1 | 2/2006 |
| WO | 2006023444 A2 | 3/2006 |
| WO | 2007048099 A2 | 4/2007 |
| WO | 2009031035 A2 | 3/2009 |
| WO | 2009071998 A2 | 6/2009 |
| WO | WO 2013/007534 A1 | 1/2013 |
| WO | WO 2013/017836 A2 | 2/2013 |

OTHER PUBLICATIONS

Ellouali, M. et al., "Antitumor Activity of Low Molecular Weight Fucans Extracted from Brown Seaweed Ascophyllum Nodosum," Anticancer Res., Nov.-Dec. 1993, pp. 2011-2020, 12 (6A).

Malette, W. G. et al., "Chitosan, a New Hemostatic," Ann Th. Surg., Jul. 1983, pp. 55-58, 36.

Langenbech, M. R. et al., "Comparison of biomaterials in the early postoperative period," Surg Endosc., May 2003, pp. 1105-1109, 17 (7).

Bracco, P. et al., "Comparison of polypropylene and polyethylene terephthalate (Dacron) meshes for abdominal wall hernia repair: A (56) References Cited

OTHER PUBLICATIONS chemical and morphological study," Hernia, 2005, pp. 51-55, 9 (1), published online Sep. 2004.

Klinge, U. et al., "Foreign Body Reaction to Meshes Used for the Repair of Abdominal Wall Hernias," Eur J. Surg, Sep. 1999, pp. 665-673, 165.

Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 14(4).

Haneji, K. et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, pp. 189-201, 52(2), published online Nov. 2009.

Junge, K. et al., "Functional and Morphologic Properties of a Modified Mesh for Inguinal Hernia Repair," World J. Surg., Sep. 2002, pp. 1472-1480, 26.

Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.

Welty, G. et al., "Functional impairment and complaints following incisional hernia repair with different polypropylene meshes," Hernia, Aug. 2001; pp. 142-147, 5.

Varum, K. et al., "In vitro degradation rates of partially N-acetylated chitosans in human serum," Carbohydrate Research, Mar. 1997, pp. 99-101, 299.

Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).

Scheidbach, H. et al., "In vivo studies comparing the biocompatibility of various polypropylene meshes and their candling properties during endoscopic total extraperitoneal (TEP) patchplasty: An experimental study in pigs," Surg. Endosc., Feb. 2004, pp. 211-220,18(2).

Blondin, C. et al., "Inhibition of Complement Activation by Natural Sulfated Polysaccharides (Fucans) from Brown Seaweed," Molecular Immuol., Mar. 1994, pp. 247-253, 31(4).

Zvyagintseva, T. et al., "Inhibition of complement activation by water-soluble polysaccharides of some far-eastern brown seaweeds," Comparative Biochem and Physiol, Jul. 2000, pp. 209-215,126(3).

Rosen, M. et al., "Laparoscopic component separation in the single-stage treatment of infected abdominal wall prosthetic removal," Hernia, 2007, pp. 435-440, 11, published online Jul. 2007.

Amid, P., "Lichtenstein tension-free hernioplasty: Its inception, evolution, and principles," Hernia, 2004; pp. 1-7, 8, published online Sep. 2003.

Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).

O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).

Muzzarelli, R. et al., "Reconstruction of parodontal tissue with chitosan," Biomaterials, Nov. 1989, pp. 598-604, 10.

Haroun-Bouhedja, F. et al., "Relationship between sulfate groups and biological activities of fucans," Thrombosis Res., Dec. 2000, pp. 453-459, 100(5).

Blondin, C. et al., "Relationships between chemical characteristics and anticomplementary activity of fucans," Biomaterials, Mar. 1996, pp. 597-603, 17(6).

Strand, S. et al., "Screening of Chitosans and Conditions for Bacterial Flocculation," Biomacromolecules, Mar. 2001, 126-133, 2.

Kanabar, V. et al., "Some structural determinants of the antiproliferative effect of heparin-like molecules on human airway smooth muscle," Br. J. Pharmacol., Oct. 2005, pp. 370-777, 146(3).

Hirano, S. et al., "The blood biocompatibility of chitosan and N-acylchitosans," J. Biomed. Mater. Res., Apr. 1985, 413-417, 19.

Rao, B. et al., "Use of chitosan as a biomaterial: Studies on its safety and hemostatic potential," J. Biomed. Mater. Res., Jan. 1997, pp. 21-28, 34.

Prokop, A. et al., "Water Soluble Polymers for Immunoisolation I: Complex Coacevation and Cytotoxicity," Advances in Polymer Science, Jul. 1998, pp. 1-51, 136.

Collins, R. et al., "Use of collagen film as a dural substitute: Preliminary animal studies," Journal of Biomedical Materials Research, Feb. 1991, pp. 267-276, vol. 25.

Preliminary Search Report from French Patent Office dated Dec. 20, 2006, 3 pages.

Australian Examination Report for application No. 2014276851 dated Mar. 16, 2018 (3 pages).

Australian Examination Report dated Jun. 27, 2018 in corresponding Australian Patent Application No. 2014276851.

* cited by examiner

TEXTILE-BASED PROSTHESIS FOR LAPAROSCOPIC SURGERY

CROSS-REFERENCE TO RELATED APPLICATIONS

This application is a National Stage Application of PCT/EP14/061655 under 35USC § 371 (a), which claims priority of French Patent Application Serial No. 13/55261 filed Jun. 7, 2013, the disclosures of each of the above-identified applications are hereby incorporated by reference in their entirety.

The present invention relates to a prosthesis based on a biocompatible textile and more particularly intended to be implanted by laparoscopy, such as, for example, the wall reinforcement prostheses for repair of hernias.

Wall reinforcement prostheses, for example for the abdominal wall, are widely used in surgery. These prostheses are intended to treat hernias by temporarily or permanently filling a tissue defect. These prostheses are generally made from a biocompatible prosthetic textile and can have a number of shapes, for example rectangular, circular or oval, depending on the anatomical structure to which they are to adapt. Some of these prostheses are made from entirely bioresorbable filaments and are intended to disappear after they have performed their reinforcing function during the period of cellular colonization and tissue rehabilitation. Others comprise non-bioresorbable filaments and are intended to remain permanently in the body of the patient.

Moreover, in order to minimize the trauma subsequent to any surgical intervention, patients are increasingly operated on by laparoscopy when the type of intervention performed allows this. Laparoscopy requires only very small incisions through which a trocar is passed, with the prosthesis being conveyed inside the trocar to the implantation site. Open surgery is thus avoided, and the patient can soon leave hospital. Laparoscopy is particularly popular in surgical interventions performed in the abdomen, for example the treatment of hernias.

However, the trocars used in laparoscopic surgery generally have a relatively small calibrated diameter, which may vary, for example, from 5 to 15 mm, in order to reduce as much as possible the size of the incision that is made. The prosthesis therefore has to be conveyed within a conduit of small diameter and must then be deployed at the implantation site.

To carry out this step, the prosthesis is generally rolled up on itself in order to make it slide in the conduit of the trocar or is introduced directly by force, if appropriate with the aid of laparoscopy forceps. However, the small diameter of the trocar used makes this step particularly difficult to carry out. If the rolling-up of the prosthesis is not correctly guided and effected, the textile may form a plug in the trocar. The prosthesis no longer slides inside the trocar, and it is very complicated to remove it from the latter. Moreover, even when the prosthesis has been correctly rolled up, the emergence of the prosthesis from the trocar and the deployment of the prosthesis at the implantation site are complex steps. Indeed, the surgeon initially has to pull on the prosthesis in order to free it from the trocar, but without damaging it. He then has to deploy the prosthesis and spread the latter out perfectly. If the prosthesis does not spread out perfectly against the abdominal wall for example, there may be a risk of a soft organ being inserted between the prosthesis and said wall, which can lead to risks of adherence, pain and intestinal occlusion and can increase the possibility of recurrence. It is therefore essential for the surgeon to ensure that no part of the prosthesis is folded and that no viscera or part of the intestine is caught between the prosthesis and the abdominal wall. However, on account of the limited space at the implantation site, it may prove complicated to deploy the prosthesis and then to orient it suitably with respect to the surrounding anatomical structures.

There is therefore still the need for a prosthesis that is based on a biocompatible textile, that can be used for the repair of hernias, that can be easily introduced into a conduit such as that of a trocar of small diameter, without damaging said textile, and that is able to be deployed completely, and preferably easily, once the implantation site in the body of the patient has been reached.

The present invention aims to meet such a need.

A first aspect of the invention concerns a prosthesis comprising:
 at least one flexible biocompatible textile having a shape defining a longitudinal axis A, and
 at least one reinforcing element for said textile,
 characterized in that said reinforcing element comprises at least one semi-rigid elongate structure connected to said textile, said structure being substantially parallel to said longitudinal axis A and having a distal end provided with at least one fastening element distinct from said textile and capable of cooperating with a part of a tool that is able to pass through said trocar, in order to temporarily couple said prosthesis to said tool.

In the present application, the longitudinal axis of a shape is understood as the axis aligned on the greatest dimension of said shape. In the case where said shape is a disc and does not have a greatest dimension, the longitudinal axis is a diameter of this disc.

In this application, the distal end of a device means the end farthest from the hand of the user, and the proximal end means the end nearest to the hand of the user. Likewise in this application, the term "distal direction" means the direction of introduction of the prosthesis into the body of the patient, and the term "proximal direction" means the direction opposite to this direction of introduction.

According to the present application, "textile" is understood as any arrangement or assembly of biocompatible yarns, fibres, filaments and/or multifilaments, for example obtained by knitting, weaving, braiding, or non-woven.

In the present application, "biocompatible" is understood as meaning that the materials having this property can be implanted in the human or animal body.

Within the meaning of the present application, a "flexible textile" is understood as a textile that can be folded up but that does not have an inherent elasticity allowing it to spontaneously recover a spread-out configuration once it has been folded up.

Within the meaning of the present application, a "semi-rigid structure" is understood as a structure having a rigidity that allows it to keep a textile spread out in the absence of any stress and to be gripped by instruments conventionally used in laparoscopic surgery, such as forceps, so as to be able to manipulate the textile, for example.

The prosthesis according to the invention is able to be easily gripped by a part of a tool conventionally used in laparoscopic surgery, for example by at least one of the jaws of a pair of forceps, and to be then introduced into a trocar by a simple distal movement towards the proximal entrance of the trocar, without first having to fold the prosthesis. The nature and the arrangement of the reinforcing element, provided with a fastening element at the distal end thereof, cause automatic folding along one or more longitudinal folds when, for example, a jaw of the forceps is engaged in the fastening element and the prosthesis is then transported towards the trocar. The forceps are then introduced into the proximal entrance of the trocar and pushed towards the distal end of the trocar. During this movement, the prosthesis is forced automatically to fold up along one or more longitudinal folds and, coupled to the forceps, it enters the trocar without difficulty. The prosthesis according to the invention could also be pushed into the trocar directly by hand by the surgeon, then by laparoscopy forceps in order to complete the introduction of the prosthesis into the abdomen of the patient, for example.

Thus, the prosthesis is able to adopt an elongate configuration, substantially aligned on its longitudinal axis A and very compact in the radial direction, allowing it to pass through a trocar without difficulty. The prosthesis can thus be folded in order to enter a trocar of small diameter, for example a diameter of 5 to 15 mm.

When the prosthesis emerges from the trocar, the surgeon can make use of the reinforcing element to deploy the prosthesis and return the latter to its initial spread-out configuration. The prosthesis is capable of conforming to the anatomical structures and of remaining in place once it has emerged from the trocar.

The textile of the prosthesis according to the invention can have any shape. The textile can have the shape of a disc, in which case one of its diameters defines the longitudinal axis A of the textile. In one embodiment, the textile has a generally elongate shape, for example a rectangular, oval or elliptic shape, defining a longitudinal axis A. The textile can have another initial shape and can then be cut to such an elongate shape, in particular to a shape adapted to the defect, for example the hernia defect, that is to be treated.

In one embodiment, said generally elongate shape is a rectangle. In another embodiment, said generally elongate shape is an ellipse. Such shapes are particularly advantageous, since they are similar to the anatomical shape of the defect that is to be filled. Moreover, such prostheses can adopt a compact shape that is substantially aligned on their longitudinal axis, permitting easy introduction into a trocar, even one of small diameter.

In one embodiment, the textile is a mesh.

Within the meaning of the present application, a "mesh" is understood as a textile, as defined above, which is openworked, that is to say provided with pores that favour recolonization of tissue. Such a mesh can be bioresorbable, permanent or partially bioresorbable. It is sufficiently flexible to be folded up at the time of introduction of the prosthesis into the trocar. Such meshes are well known to a person skilled in the art.

In one embodiment of the invention, the mesh is a knit. By virtue of the meshwork of the knit, it is possible to obtain openworked faces that promote cell recolonization after implantation. The knit can be two-dimensional or three-dimensional.

Within the meaning of the present application, a two-dimensional knit is understood as a knit having two opposite faces linked to each other by meshes but devoid of a spacer giving it a certain thickness: such a knit can be obtained, for example, by knitting yarns on a warp knitting machine or raschel knitting machine using two guide bars. Examples of knitting two-dimensional knits suitable for the present invention are given in the document WO2009/071998.

According to the present application, a three-dimensional knit is understood as a knit having two opposite faces linked to each other by a spacer that gives the knit a significant thickness, said spacer itself being formed from additional linking yarns in addition to the yarns forming the two faces of the knit. Such a knit can be obtained, for example, on a double-bed warp knitting or raschel knitting machine using several guide bars. Examples of knitting three-dimensional knits suitable for the present invention are given in the documents WO99/05990, WO2009/031035 and WO2009/071998.

The reinforcing element comprises at least one semi-rigid elongate structure connected to the textile, said structure being substantially parallel to said longitudinal axis A.

The materials that may be suitable for producing the reinforcing element, in particular said structure, of the prosthesis according to the invention may be chosen from any biocompatible material having a certain rigidity in order to meet the requirements described above.

In one embodiment, said reinforcing element is made of bioresorbable material. In the present application, "bioresorbable" or "biodegradable" is understood to mean that the materials having this property are absorbed and/or degraded by the tissues or washed from the implantation site and disappear in vivo after a certain time, which may vary, for example, from a few hours to a few months, depending on the chemical nature of the materials.

Thus, the reinforcing element acts as a guide for the prosthesis for introducing the latter into a trocar, then acts as a means of stiffening the prosthesis during the positioning and implanting of the prosthesis, after which it gradually degrades, for example when the prosthesis has been fixed or when the textile has been recolonized by the surrounding cells.

For example, the bioresorbable material can be chosen from among polylactic acid (PLA), polycaprolactones (PCL), polydioxanones (PDO), trimethylene carbonates (TMC), polyvinyl alcohol (PVA), polyhydroxyalkanoates (PHA), oxidized cellulose, polyglycolic acid (PGA), copolymers of these materials and mixtures thereof. For example, the bioresorbable material can be a copolymer of polylactic acid and of polyglycolic acid.

Alternatively, the reinforcing element of the prosthesis according to the invention is made of a non-bioresorbable material chosen from among polypropylenes, polyesters such as polyethylene terephthalates, polyamides, silicones, polyether ether ketone (PEEK), polyarylether ether ketone (PAEK), polyurethanes and mixtures thereof.

In another embodiment, the reinforcing element is formed by a combination of bioresorbable material and of non-bioresorbable material.

The reinforcing element, in particular said structure, of the prosthesis according to the invention is connected to said textile. For example, the reinforcing element can be fixed to the textile by sewing, ultrasonic welding, or else by adhesive bonding or moulding.

In one embodiment, the reinforcing element of the prosthesis according to the invention is moulded over the textile. Thus, the reinforcing element is connected to the textile by injection moulding of one or more thermoplastic or thermosetting biocompatible materials. For example, the mould of an injection-moulding machine is equipped with an insert gate in which the textile is held. One or more thermoplastic or thermosetting biocompatible materials are then heated to their melting point and injected into the mould, the latter having one or more channels of the shape desired for the reinforcing element. The holding of the textile, the precision of the injection volume and the choice of the injection parameters make it possible to obtain a reinforcing element without material loss, without flash and with good surface evenness. Such a method allows the reinforcing element to be fixed to the textile in a particularly effective and lasting way.

In one embodiment, the reinforcing element is obtained by moulding a copolymer of polylactic acid and of polyglycolic acid over the textile.

The semi-rigid elongate structure of the reinforcing element of the prosthesis according to the invention has a distal end provided with at least one fastening element distinct from said textile.

The fastening element of the prosthesis according to the invention is capable of cooperating with a part of a tool that is able to pass through said trocar, in order to temporarily couple said prosthesis to said tool. Thus, the fastening element can have any shape suitable for the engagement of a part of a tool that is able to pass through a trocar. For example, with the tool being intended to carry the prosthesis along with it in the distal direction, the fastening element can have any shape allowing an element, for example a projecting element, of the tool to be engaged in the fastening element when the tool is brought towards the fastening element by a distal movement.

The fastening element is preferably dimensioned so as to be able to receive a projecting element of a laparoscopy tool, for example a jaw of a pair of forceps, that can pass through a trocar of small diameter, for example a diameter of 10-15 mm, and also so as to be able itself to pass easily through the trocar when provided with the prosthesis. Thus, for example, for use of the prosthesis according to the invention with a trocar having an internal diameter of 15 mm, the fastening element has outer dimensions smaller than a circle with a diameter of 15 mm, preferably smaller than a circle with a diameter of 5 mm.

The present invention thus relates to a prosthesis comprising:
   at least one flexible biocompatible textile having a shape defining a longitudinal axis A, and
   at least one reinforcing element for said textile,
   characterized in that said reinforcing element comprises at least one semi-rigid elongate structure connected to said textile, said structure being substantially parallel to said longitudinal axis A and having a distal end provided with at least one fastening element distinct from said textile, said fastening element having outer dimensions smaller than a circle with a diameter of 15 mm, preferably smaller than a circle with a diameter of 5 mm.

The fastening element is distinct from the textile. Thus, when the tool is engaged in the fastening element, said tool is not in contact with the textile, and the risks of the textile being damaged, for example by being caught by a projecting part of the tool, are avoided. Therefore, the integrity of the structure of the textile, in particular its openworked structure for example, is not affected when the tool is coupled to the prosthesis.

In one embodiment, the fastening element has the shape of a closed ring. Thus, for example, a jaw of a pair of forceps for a trocar can be easily engaged in said ring. This engagement makes it possible to couple the prosthesis to the forceps and to introduce the prosthesis into the trocar at the same time as the forceps, for example once the two jaws have been closed on each other.

In one embodiment, said fastening element has the shape of an open ring, the opening in the ring being situated substantially in the proximal region of the ring. Thus, when a part of the tool, for example a projecting element such as the jaw of a pair of forceps, approaches the fastening element via a distal movement with respect to the prosthesis, it can be engaged in the open ring. When the user continues the distal movement of the tool with respect to the prosthesis, the jaw engaged in the open ring comes into abutment against the non-open part of the ring, and the prosthesis is thereby coupled to the tool and is carried along with the tool in the distal direction.

In one embodiment, said structure comprises at least one rod segment extending parallel to the longitudinal axis A. Thus, during the introduction of the prosthesis into the trocar, the rod segment serves as a guide for the natural folding of the textile of the prosthesis along one or more longitudinal folds parallel to the rod segment.

In one embodiment, the reinforcing element comprises several of said structures parallel to one another, each being provided, at the distal end thereof, with a said fastening element. For example, said fastening elements are aligned along a line transverse to said longitudinal axis A. The surgeon can thus successively engage the different fastening elements with the same jaw of a pair of forceps, thereby obtaining a first folding of the textile along one or more longitudinal folds, before introducing the prosthesis into the trocar.

In one embodiment, said structure additionally comprises one or more oblique rod segments configured to promote the folding of the textile along one or more longitudinal folds when the textile is subjected to a radial pressure in the direction of its longitudinal axis A. For example, the oblique rod segments can be situated generally in a proximal region of the textile and can form an angle of 0 to 50° with the longitudinal axis A, converging towards a rod segment parallel to the longitudinal axis situated in a distal region of the textile. Such an elongate structure allows the prosthesis to be folded up gradually as it enters the trocar, the two oblique rod segments serving as a guide for the textile as it folds up inside the trocar when the textile is subjected to the radial pressure acting in the direction of its longitudinal axis A and exerted by the walls of the trocar.

In one embodiment, the prosthesis additionally comprises an indicator of a defined location of the textile. For example, the prosthesis can comprise an indicator of the centre of the textile. The centre of the textile can be the centre of the prosthesis. Such an indicator can help the surgeon when placing the prosthesis in the implantation site, the visibility at such a site generally being reduced and/or obstructed by the presence of the surrounding organs. Such an indicator can be in the form of a geometric figure. In one embodiment, said indicator forms a part of said elongate structure.

In one embodiment, the prosthesis comprises a means of information concerning the orientation of the prosthesis. Thus, at the implantation site where the visibility is reduced, the surgeon can have information concerning the longitudinal or transverse direction of the prosthesis. In one embodiment, said means of information forms a part of said elongate structure.

In one embodiment of the invention, one face of the textile is covered by a non-stick coating.

Such a non-stick coating makes it possible in particular to avoid the formation of undesired and serious post-surgical fibrous adhesions.

Within the meaning of the present application, "non-stick" is understood as a smooth and non-porous biocompatible material or coating that does not offer space for cell recolonization and that preferably promotes the growth of new peritoneum.

Another aspect of the present invention is a method by which a prosthesis of the kind described above is conveyed to an implantation site, said method comprising the following steps:

a part of a tool that is able to pass through a trocar is engaged in the one or more fastening elements in order to couple the prosthesis to said tool, the prosthesis is transported to the proximal entrance of the trocar by a distal movement of the tool, said tool, coupled to the prosthesis, is introduced into the proximal orifice of the trocar, and said tool and the prosthesis inside the trocar are pushed by a distal force directed along the longitudinal axis of the trocar.

The prosthesis is thus pushed along the longitudinal axis of the trocar until its end, along with said tool, emerges from the trocar via the distal orifice thereof.

The push is continued until the whole prosthesis has emerged completely from the trocar.

By virtue of the structure of the prosthesis according to the invention, the step of introducing the prosthesis into the trocar is greatly facilitated. Likewise, with the prosthesis folding up automatically into a compact configuration as it penetrates into the proximal orifice of the trocar, it passes through the trocar easily and without damage.

Finally, the prosthesis is returned to its spread-out configuration at the implantation site by the surgeon unfolding the prosthesis. To do this, the surgeon can make use of the reinforcing element, which allows the unfolded prosthesis to be maintained in a spread-out state in the absence of any external stress.

The advantages of the present invention will become clearer from the following detailed description and from the attached drawings in which.

Figure 1:
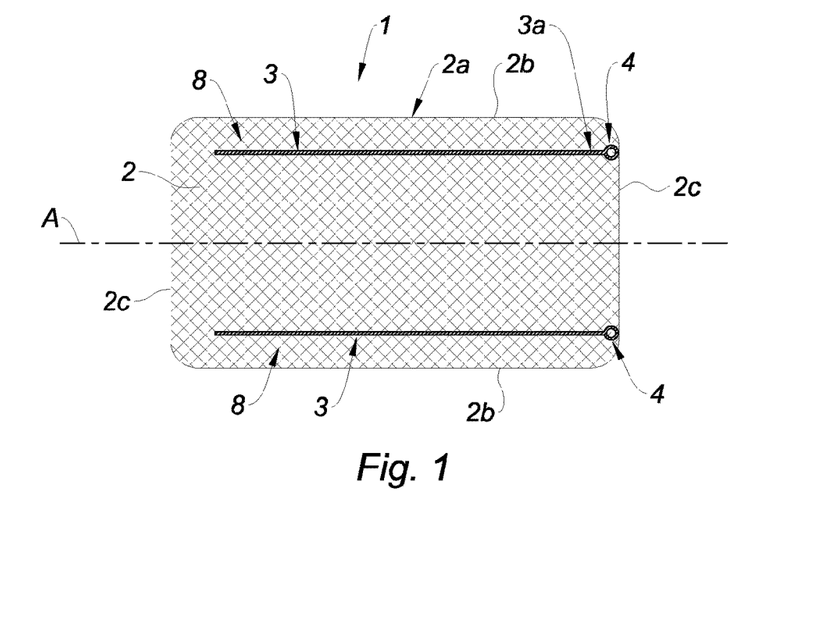
FIG. 1 shows a plan view of a first embodiment of a prosthesis according to the invention.

FIG. 1 shows an embodiment of a prosthesis 1 according to the invention. The prosthesis 1 comprises a biocompatible textile 2 and a reinforcing element in the form of two semi-rigid elongate structures 8. Each elongate structure 8 comprises a rod segment 3 provided with a fastening element, in the form of a closed ring 4, at the distal end 3a thereof.

As will be seen from FIG. 1, the textile 2 has a generally elongate shape defining a longitudinal axis A. In another embodiment, the textile could have the shape of a disc, in which case one of the diameters of the disc would define the longitudinal axis of the textile.

Referring to FIG. 1, the textile 2 is thus delimited by a peripheral outer edge 2a forming substantially two opposite long sides 2b, which are substantially parallel to the longitudinal axis A, and two opposite short sides 2c, which are substantially perpendicular to the longitudinal axis A. In the example shown, the textile 2 has the general shape of a rectangle. Such an embodiment is suitable for the repair of a hernia of the abdominal wall, for example.

In other embodiments, the textile 2 could have an oval shape, or an elliptic shape, or be protean.

The textile 2 is made up of an arrangement of biocompatible filaments, such as a knit, a woven or a nonwoven. Preferably, as is shown in FIG. 1, the textile 2 is in the form of a mesh, that is to say it has openings for better tissue integration. For example, the textile 2 can be a two-dimensional or three-dimensional knit. Such textiles in the form of meshes or knits are well known to a person skilled in the art and are not described in any greater detail here.

The textile 2 can be bioresorbable, permanent or partially bioresorbable. As will become clear from the description below, the textile 2 is sufficiently flexible to be folded up, in particular at the time of introduction of the prosthesis into a trocar, along one or more longitudinal folds. In general, however, the textile 2 does not have an inherent elasticity allowing it to spontaneously recover a spread-out configuration once it has been folded up. The textile 2 can be supplied in the form of a band, which one cuts to the dimensions of the defect to be treated.

Referring again to FIG. 1, and as will become clear on reading the description below, the elongate structures 8 are parallel to each other and parallel to the longitudinal axis A. The rod segments 3 serve as an element for reinforcing the textile 2, in order to stiffen the latter and keep it in a substantially spread-out state in the absence of any external stress, as shown in FIG. 1, and also as a tool permitting both the manipulation of the textile 2 and the guiding of the prosthesis 1 upon introduction of the latter into a trocar, and also as a tool for assisting in the deployment of the prosthesis 1 when the latter emerges from the trocar at the implantation site. For this purpose, the elongate structures, in particular the rod segments 3, are connected to the textile 2 and have a rigidity allowing them to keep the textile 2 in its substantially spread-out state in the absence of any external stress, and allowing them to be gripped by a tool conventionally used in laparoscopic surgery, such as forceps intended to pass through a trocar.

The elongate structures 8, in particular the rod segments 3, are connected to the textile 2. They can be attached to the textile 2 by means of a seam, or else by means of an ultrasonic weld, by adhesive bonding, or by injection moulding.

In one embodiment, the rod segments 3 are joined to the textile by means of injection moulding. Such an embodiment makes it possible to secure the fixing of the rod segments 3 to the textile 2 in a particularly effective manner and to produce the prostheses according to the invention at an industrial scale.

In the technique of injection moulding, a mould is formed in which, for example with reference to the example shown in FIG. 1, a cavity is provided that is formed by two channels corresponding to the two rod segments 3 that are to be obtained, these two channels being parallel to each other. The textile is held in an insert gate of the mould, the long sides 2b of its peripheral outer edge 2a being parallel to the two channels. The thermoplastic material used to produce the rod segments, for example a copolymer of polylactic acid and of polyglycolic acid, is heated and injected into these channels using an injection moulding machine.

After the injection step, the mould is opened and the prosthesis 1 is withdrawn from the mould. Such a method allows the textile to be "embedded" in the part moulded over it. Thus, the rod segments 3, which are the overmoulded parts, are connected to the textile 2, without any risk of their coming loose or fragmenting.

On account of the nature and the structure of the rod segments 3, the latter act as guides for introducing the prosthesis 1 into a small orifice, such as an admission orifice of a trocar, as will become clear from the description below.

Figure 2:
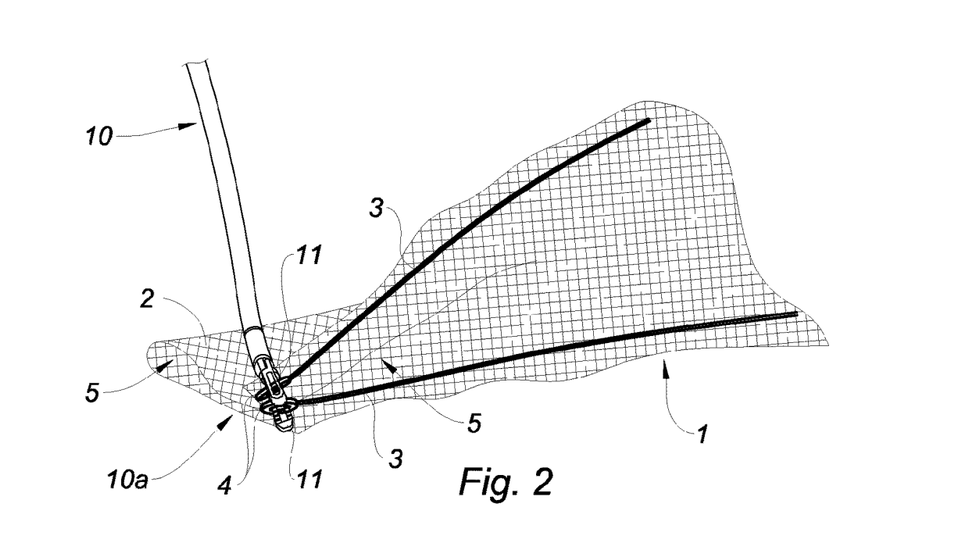
FIG. 2 shows a view of a step during which a jaw of a pair of forceps able to pass through a trocar is engaged in the fastening elements of the prosthesis of FIG. 1.
Figure 3:
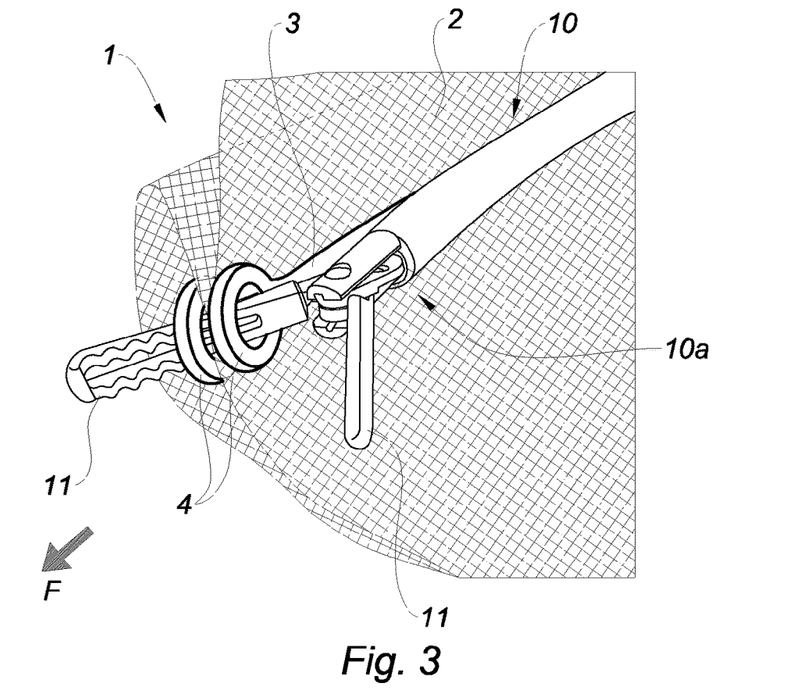
FIG. 3 is a view, on an enlarged scale, of a jaw of a pair of forceps being engaged in the fastening elements of the prosthesis of FIG. 1.

Thus, in order to easily introduce the prosthesis 1 of FIG. 1 into a trocar, the user makes use of a tool that is able to pass through a trocar, for example forceps 10 as shown in FIGS. 2 and 3. Referring to these figures, the forceps 10 are provided, at the distal end 10a thereof, with two jaws 11 that are capable of opening and closing in order to release or, by contrast, imprison a component. The user holds the forceps 10 with the two jaws open and engages one 11 of these two jaws successively into each of the two rings 4 present at the respective distal ends 3a of the rod segments 3 (see FIG. 3). On doing this, as shown in FIG. 2, one or more longitudinal folds 5 are created in the textile 2. Depending on the number of rod segments 3 present, the textile 2 can form one or more longitudinal folds 5, like an accordion.

In the example shown, the fastening element is a closed ring 4. It is clear from FIG. 3 that such a closed ring 4 could be replaced by an open ring (not shown), of which the opening would be situated in the proximal region of the ring. Indeed, since the forceps 10 are intended to be moved in the distal direction once coupled to the prosthesis 1, the absence of material in the proximal region of the ring does not prevent the effective coupling of the prosthesis to the forceps and the transport of the prosthesis in the distal direction by the tool, once the latter has been coupled to the prosthesis.

The ring 4 is dimensioned so as to be able to receive a jaw of a pair of forceps, that can pass through a trocar of small diameter, for example a diameter of 5-15 mm, and also so as to be able itself to pass easily through the trocar. Thus, for example, for using the prosthesis according to the invention with a trocar having an internal diameter of 5-15 mm, the ring 4 has an external diameter of less than 10 mm, for example of approximately 5 mm.

The fastening element, i.e. the closed ring 4 in the example shown, is distinct from the textile 2. The ring 4 is not moulded on the textile 2. This is because the ring 4 has to be able to receive a projecting element of a tool for laparoscopic surgery, in order to be able to couple the prosthesis to said tool, but said projecting element must not engage the textile 2 itself. Thus, when the tool is engaged in the ring 4, said tool is not in contact with the textile 2, and the risks of the textile 2 being damaged, for example by being caught by a projecting part of the tool, are avoided. Therefore, the integrity of the structure of the textile, in particular its openworked structure when the textile is a mesh for example, is not affected when the tool is coupled to the prosthesis.

Referring to FIGS. 2 and 3, it is clear that the jaw 11 engaged in the two rings 4 is not in contact with the textile 2 and, therefore, does not risk damaging the latter. As is shown in FIG. 3, the forceps 10 can be arranged in a position in which they are substantially aligned on the rod segments 3.

Thus, when a user moves the forceps 10 in the distal direction symbolized by the arrow F in FIG. 3, the prosthesis 1 is transported along with the forceps 10 in this same direction. The user then introduces the distal end 10a of the forceps 10 into the proximal entrance (not shown) of the trocar 12 shown in FIG. 4. As the user gradually pushes the distal end 10a of the forceps 10 inside the trocar 12 in the distal direction, the textile 2 is guided by the rod segments 3, which are semi-rigid, and it folds up along one or more longitudinal folds similar to the longitudinal folds 5 of FIG. 2 and aligned on the rod segments 3. Thus, the prosthesis 1 adopts a compact configuration that allows it to easily pass through the trocar 12. The rod segments 3 serve as guide elements for the folding of the prosthesis 1 along longitudinal folds.

Figure 4:
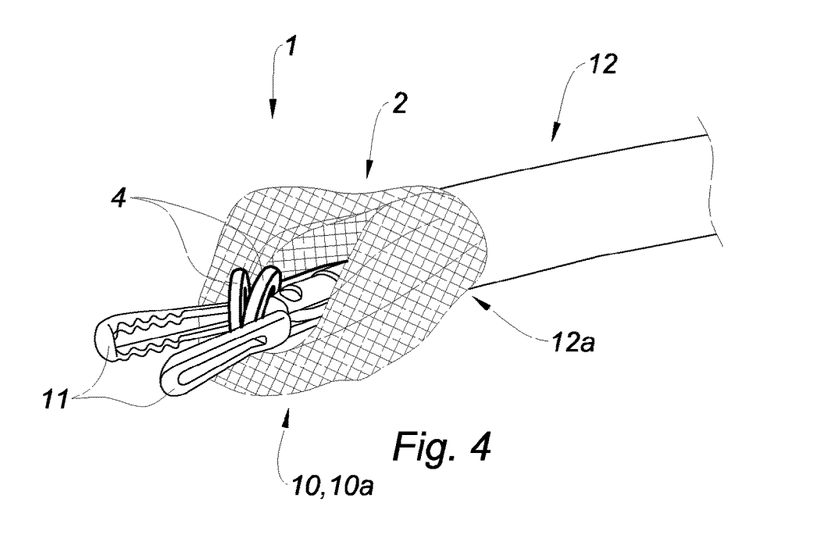
FIG. 4 is a view of the forceps of FIG. 2 engaged in the fastening elements of the prosthesis of FIG. 1 on emergence from the trocar.

FIG. 4 shows the distal end 10a of the forceps 10 after passage through the trocar 12, at the moment when the forceps emerge from the trocar 12 via the distal end 12a thereof. The textile 2 is coupled to a jaw 11 of the forceps 10 by engagement of the rings 4 in this jaw 11. The user continues to push the forceps 10 in the distal direction until the whole prosthesis 1 has emerged completely from the trocar 12. The user then uncouples the prosthesis 1 from the jaw 11 of the forceps 10, and he is then able to deploy the prosthesis 1 with the aid of the rod segments 3 in order to keep the textile 2, and therefore the prosthesis 1, in a spread-out state.

The prosthesis 1 is then ready to be positioned opposite a hernia defect that is to be treated. During the positioning of the prosthesis 1, the latter can be easily manipulated by means of tools conventionally used in laparoscopic surgery, these tools being able, among other things, to take hold of all or some of the elongate structures 8.

Figure 5:
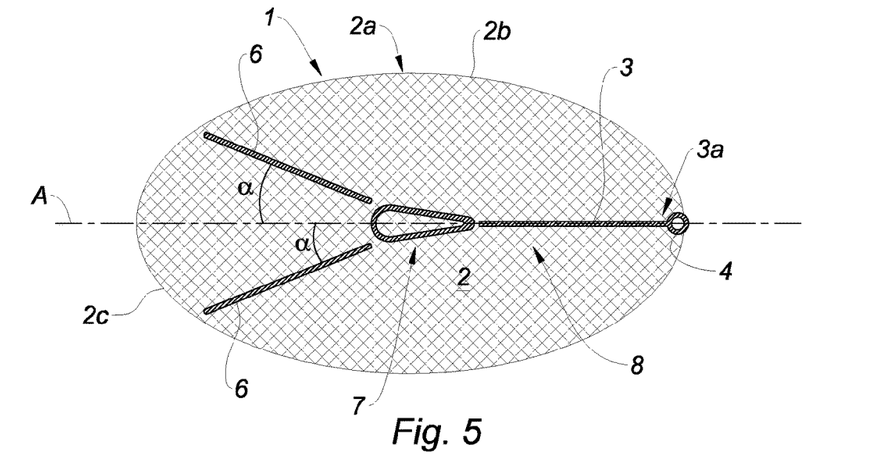
FIG. 5 is a plan view of a second embodiment of the prosthesis according to the invention.
Figure 6:
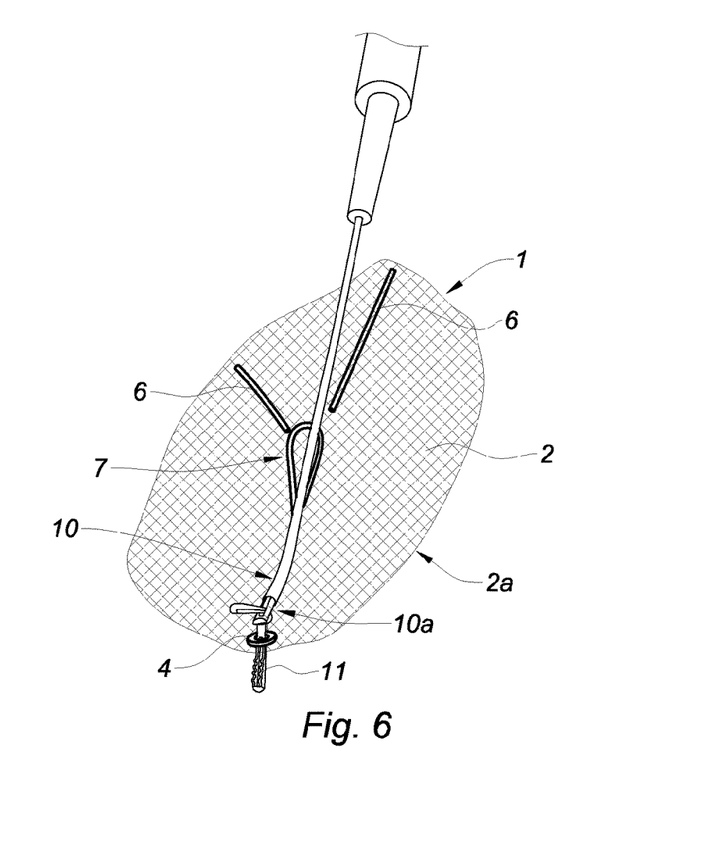
FIG. 6 is a plan view showing a step during which a jaw of a pair of forceps able to pass through a trocar is engaged in the fastening element of the prosthesis of FIG. 5.

FIGS. 5 and 6 show another embodiment of the prosthesis 1 according to the invention, in which the textile 2 has generally the shape of an ellipse defining a longitudinal axis A. As in the preceding embodiment, the textile 2 is delimited by a peripheral outer edge 2a forming substantially two opposite long sides 2b, which are substantially parallel to the longitudinal axis A, and two opposite short sides 2c, which are substantially perpendicular to the longitudinal axis A. An ellipse shape of this kind is suitable for the repair or a hernia of the abdominal wall, for example.

In this embodiment, the reinforcing element comprises a semi-rigid elongate structure 8 comprising a rod segment 3, which is generally aligned on the longitudinal axis A and which is provided with a fastening element in the form of a closed ring 4 at the distal end 3a thereof. The rod segment 3 is situated in the distal region of the textile 2 and, therefore, of the prosthesis 1. The structure 8 additionally comprises two oblique rod segments 6, which each form an angle α with the longitudinal axis A and are generally situated proximally with respect to the proximal end of the rod segment 3. Finally, the elongate structure 8 also comprises a triangular frame 7 extending in the longitudinal direction and arranged between the rod segment 3 and the oblique rod segments 6. Such a shape of the structure 8 facilitates the automatic folding of the textile 2 along longitudinal folds at the moment when the textile 2, coupled to trocar forceps, is introduced into a trocar.

Furthermore, the triangular frame 7 forms an indicator of the centre of the textile 2 and also a means of information concerning the orientation of the prosthesis 1. This is because the triangular frame 7 itself is of elongate shape and indicates to the surgeon the longitudinal direction of the prosthesis 1. Finally, the short side of the triangular frame 7 indicates the proximal direction, while the angle opposite this short side indicates to the surgeon the distal direction. Such an indicator of a defined location of the textile and a such means of information concerning the prosthesis are particularly useful to the surgeon when the prosthesis 1 has reached the implantation site, where the field of view is reduced and/or obstructed by the presence of the surrounding organs.

FIG. 6 shows the step in which a jaw 11 of a pair of forceps 10 is coupled to the textile 2, and therefore to the prosthesis 1, with a view to introducing the prosthesis 1 into a trocar (not shown).

The prosthesis according to the invention can thus be easily introduced into a trocar, without any risk of forming a plug inside the trocar. By virtue of its nature and its structure, the reinforcing element of the prosthesis according to the invention stiffens the prosthesis and serves as an element for guiding and transporting the prosthesis inside a trocar conduit of particularly small diameter, such as a diameter of 5-15 mm. The reinforcing element, by stiffening the textile of the prosthesis, also serves to spread the prosthesis out at the moment when the latter emerges from the trocar at the implantation site.

The invention claimed is:

1. A prosthesis intended to be conveyed to an implantation site with the aid of a trocar, comprising:
    at least one flexible biocompatible textile having two opposite faces and a shape defining a longitudinal axis, and
    at least one reinforcing element for said textile, the reinforcing element comprising at least one semi-rigid elongate rod segment situated in a distal region of the textile, one or more oblique rod segments situated in a proximal region of the textile and a triangular frame arranged between the elongate rod segment and the oblique rod segment, the at least one semi-rigid elongate rod segment fixed to at least one face of the two opposite faces of the textile and extending substantially parallel to the longitudinal axis along the at least one face, the rod segment having a proximal end and a distal end, the distal end provided with at least one fastening element having a shape of a ring and distinct from the textile, the fastening element configured to cooperate with a part of a tool that is able to pass through the trocar, in order to temporarily couple the prosthesis to the tool, wherein the one or more oblique rod segments are situated proximally to the proximal end of the at least one rod segment.

2. The prosthesis according to claim 1, wherein the biocompatible textile is a two-dimensional knit mesh.

3. The prosthesis according to claim 1, wherein the biocompatible textile is a three-dimensional knit mesh.

4. The prosthesis according to claim 1, wherein the fastening element has a shape of a closed ring.

5. The prosthesis according to claim 1, wherein the fastening element has a shape of an open ring, wherein an opening in the open ring is situated substantially in a proximal region of the open ring.

6. The prosthesis according to claim 1, wherein the fastening element comprises a bioresorbable material.

7. The prosthesis according to claim 6, wherein the bioresorbable material is selected from the group consisting of polylactic acid, polycaprolactone, polydioxanones, trimethylene carbonates, polyvinyl alcohols, polyhydroxyalkanoates, oxidized cellulose, polyglycolic acid, and mixtures thereof.

8. The prosthesis according to claim 1, wherein the fastening element comprises a non-bioresorbable material.

9. The prosthesis according to claim 8, wherein the non-bioresorbable material is selected from the group consisting of polypropylenes, polyethylene terephthalates, polyamides, silicones, polyether ether ketones, polyarylether ether ketone, polyurethanes, and mixtures thereof.

10. The prosthesis according to claim 1, wherein the fastening element comprises a copolymer of polylactic acid and polyglycolic acid.

11. The prosthesis according to claim 1, wherein the one or more oblique rod segments are configured to promote folding of the textile along one or more longitudinal folds when the textile is subjected to a radial pressure in a direction of the longitudinal axis.

12. The prosthesis according to claim 1, comprising a plurality of the oblique rods situated generally in the proximal region of the biocompatible textile converging towards the proximal end of the at least one elongate rod segment situated in the distal region of the biocompatible textile.

13. The prosthesis according to claim 1, wherein the triangular frame forms an indicator of a defined location of the textile.

14. The prosthesis according to claim 13, wherein the indicator is positioned at a center of the textile.

15. The prosthesis according to claim 13, wherein the indicator forms a part of the reinforcing element.

16. The prosthesis according to claims 1, wherein the triangular frame forms a means of information concerning an orientation of the prosthesis.

17. The prosthesis according to claim 16, wherein the means of information forms a part of the reinforcing element.

18. The prosthesis according to claim 1, wherein the reinforcing element is molded over the textile.

19. The prosthesis according to claim 1, wherein one face of the biocompatible textile comprises a non-stick coating.

20. A method of conveying a prosthesis to an implantation site comprising:
    providing a prosthesis including at least one flexible biocompatible textile having two opposite faces and a shape defining a longitudinal axis and at least one reinforcing element for said textile, the reinforcing element comprising at least one semi-rigid elongate rod segment situated in a distal region of the textile, one or more oblique rod segments situated in a proximal region of the textile and a triangular frame arranged between the elongate rod segment and the oblique rod segment, the at least one semi-rigid elongate rod segment fixed to at least one face of the two opposite faces of the textile and extending substantially parallel to the longitudinal axis along the at least one face, the rod segment having a proximal end and a distal end, the distal end provided with at least one fastening element having a shape of a ring and distinct from the textile, wherein the one or more oblique rod segments are situated proximally to the proximal end of the at least one rod segment,
    engaging the one or more fastening elements with a part to a tool thereby coupling the prosthesis to the tool via the fastening elements,
    introducing the part of the tool coupled to the prosthesis into a proximal orifice of a trocar causing the prosthesis to automatically fold into a compact configuration as the tool and the prosthesis penetrates into the proximal orifice of the trocar, and
    passing the prosthesis through a distal orifice of the trocar to the site of implantation wherein the prosthesis unfolds from the compact configuration to a spread-out configuration.

21. A prosthesis intended to be conveyed to an implantation site with the aid of a trocar, comprising:

at least one flexible biocompatible textile having two opposite faces and a shape defining a longitudinal axis, and at least one reinforcing element connected to at least one face of the two opposite faces of the textile, the reinforcing element comprising at least one semi-rigid elongate structure aligned on the longitudinal axis, one or more oblique rod segments situated at angle relative to the longitudinal axis and a triangular frame arranged between the elongate structure and the oblique rod segment, the rod segment having a proximal end and a distal end, the distal end provided with at least one fastening element having a shape of a ring and distinct from the textile, the fastening element configured to cooperate with a part of a tool that is able to pass through the trocar, in order to temporarily couple the prosthesis to the tool, wherein the one or more oblique rod segments are situated proximally to the proximal end of the at least one rod segment.

* * * * *